United States Patent
Atilio Los (10) Patent No.: US 11,090,277 B2
(45) Date of Patent: Aug. 17, 2021

(54) PREMIXTURE AND PHARMACEUTICAL COMPOSITION FOR THE ORAL ADMINISTRATION OF MEMANTINE AS A PERMANENT SUSPENSION OR ONE PREPARED PRIOR TO ADMINISTERING TO THE PATIENT AND OPTIONALLY BY ENTERAL FEEDING TUBE AND CORRESPONDING PROCEDURES

(71) Applicants: LABORATORIOS BAGÓ S.A., Buenos Aires (AR); Eastbrand Holding GMBH, Vienna (AT)

(72) Inventor: Mario Atilio Los, Buenos Aires (AR)

(73) Assignees: LABORATORIOS BAGÓ S.A., Buenos Aires (AR); Eastbrand Holding GMBH, Vienna (AT)

( * ) Notice: Subject to any disclaimer, the term of this patent is extended or adjusted under 35 U.S.C. 154(b) by 0 days.

(21) Appl. No.: 16/064,506

(22) PCT Filed: Dec. 23, 2015

(86) PCT No.: PCT/IB2015/059926
§ 371 (c)(1),
(2) Date: Jun. 21, 2018

(87) PCT Pub. No.: WO2017/109547
PCT Pub. Date: Jun. 29, 2017

(65) Prior Publication Data
US 2019/0015357 A1    Jan. 17, 2019

(51) Int. Cl.
| *A61K 31/13* | (2006.01) |
| *A61K 9/00* | (2006.01) |
| *A61K 9/16* | (2006.01) |
| *A61K 9/20* | (2006.01) |
| *A61K 9/50* | (2006.01) |
| *A61P 25/28* | (2006.01) |

(52) U.S. Cl.
CPC ............ *A61K 31/13* (2013.01); *A61K 9/0056* (2013.01); *A61K 9/0095* (2013.01); *A61K 9/1611* (2013.01); *A61K 9/1623* (2013.01); *A61K 9/1652* (2013.01); *A61K 9/1664* (2013.01); *A61K 9/1682* (2013.01); *A61K 9/2009* (2013.01); *A61K 9/2018* (2013.01); *A61K 9/2059* (2013.01); *A61K 9/2068* (2013.01); *A61K 9/2081* (2013.01); *A61K 9/5026* (2013.01); *A61K 9/5073* (2013.01); *A61P 25/28* (2018.01)

(58) Field of Classification Search
None
See application file for complete search history.

(56) References Cited

U.S. PATENT DOCUMENTS

| 8,541,024 B2 * | 9/2013 | Ono ........................ A61J 3/005 424/464 |
| 2006/0024335 A1 * | 2/2006 | Roger .................. A61K 9/0056 424/400 |

FOREIGN PATENT DOCUMENTS

| EP | 1908748 A1 | 4/2008 |
| WO | WO-2006/138227 A1 | 12/2006 |
| WO | WO-2008/005534 A2 | 1/2008 |
| WO | WO-2009/084017 A2 | 7/2009 |

* cited by examiner

*Primary Examiner* — John Pak
*Assistant Examiner* — Daniel L Branson
(74) *Attorney, Agent, or Firm* — Julie K. Staple; Dinsmore & Shohl LLP (57) ABSTRACT

Pharmaceutical composition of memantine for administering orally which comprises a premixture comprising:
  i) between 74 and 85% w/w total of the premixture of a granulate of pellets comprising memantine between 10 and 15% w/w total of the premixture; coated by first coating of polyvinylpyrrolidone and a second coating comprising between 80 and 95% w/w total of the coating of cationic copolymer of dimethylaminoethyl methacrylate, butyl methacrylate and methyl methacrylate and between 5 and 20% w/w total of the coating of magnesium stearate;
  ii) between 4 and 7% w/w total of the premixture of sucralose;
  iii) between 11 and 19% w/w total of the premixture of essences.

All the components have a particle size smaller than 710 microns. The composition can be a suspension, a powder for preparing a suspension or an oral disintegrating tablet. It can also be used to be administered through a nasogastric tube.

23 Claims, 2 Drawing Sheets

PREMIXTURE AND PHARMACEUTICAL COMPOSITION FOR THE ORAL ADMINISTRATION OF MEMANTINE AS A PERMANENT SUSPENSION OR ONE PREPARED PRIOR TO ADMINISTERING TO THE PATIENT AND OPTIONALLY BY ENTERAL FEEDING TUBE AND CORRESPONDING PROCEDURES

FIELD OF THE INVENTION

This invention relates to a pharmaceutical composition containing memantine for the treatment of Alzheimer type dementia. The composition does not have the characteristic bitter taste of memantine, it is easy to swallow thanks to the small size of the particles in suspension and the absence of unpleasant aggregates when the composition is placed in the buccal cavity.

The composition is administered preferably in the form of an oral suspension and optionally it can also be administered by tubes to patients who are usually fed through an enteral feeding tube without causing obstruction problems therein.

Following preparation of a specific premixture, typically used for the various compositions according to the invention, the pharmaceutical composition is prepared and it can be presented, as preferred, in the form of a permanent suspension, powder for preparing the oral suspension and even as quickly disintegrating tables for forming a suspension in a small volume of water before administration or optionally with the saliva existing in the buccal cavity.

The specific premixture determines the characteristics of the composition according to the invention and ensures that 90% of the particles in suspension containing memantine and which go into the buccal cavity have an average diameter less than 170 microns (μm, also called micras in Spanish) and 50% of these particles have an average diameter less than 60 microns, and also they do not cause discomfort in the buccal cavity and aid the patient's swallowing.

Generally geriatric patients or those with mental problems such as dementia or Alzheimer, often have difficulty in swallowing solid dosage shapes. The absence of uncomfortable particles in the buccal cavity and the pleasant taste add to the acceptance by the patient with Alzheimer and also swallowing or dysphagia problems.

The composition is easily fractionated and has flexible posology for starting the treatment with the lowest indicated doses, and allowing the posology to be modified when necessary,

STATE OF THE ART

Oral administration is the most comfortable and most widely used method internationally for administering medicines. However, in certain cases administering traditional oral tablets may not be the most effective form of administration. The condition of dysphagia or difficulty in swallowing which occurs in many patients is one of the factors that prevents the correct swallowing of medicines in the form of tablets. Dysphagia is defined generally as the difficulty in passing food from the mouth to the stomach. It is caused by various disorders such as: structural alternations, functional disorders that obstruct the propulsion of the ball of food, oropharyngeal reconfiguration during the swallowing or the opening of the upper oesophagus sphincter.

Various studies highlight the importance of this pathology. They include:

A study from the USA during 2004 on a national level (USA TODAY—Society for the Advancement of Education—October 2004) showed that:
a) 40% of the adult population has problems in swallowing tablets, even when they have no difficulty in swallowing food normally,
b) this causes a certain index of delay in taking medicines in 14% of patients.
c) 6% of the regular dosage is lost.
d) there is a treatment abandonment rate of around 4%.

Another study in Norway during 1995 (Anderson O. et al—Tidsskr Nor Laegerfore 115-947, 949) on 6158 general medicine patients highlights that approximately 26% of patients did not take the prescribed medication due to problems associated with swallowing and caused by the size of the tablet, tablet surface or taste. Bhaty P. Badgujar et al (Acta Phar. 61 (2011), 117-139 mention that the difficulty in swallowing or dysphagia can affect 35% of the general population that is not sick. According to other authors, with ageing, swallowing problems can affect between 70 to 90% of people (J. Hernández Martin et al. Farm. Hosp. 2013; 37 (3): 198-208) and it is particularly important in patients with neurological problems. Cook I. J., Kahrillas P J AGA, Technical review on management of oropharyngeal dysphagia. Gastroenterology 1999; 116: 455-78 describes that swallowing problems or dysphagia affect 84% of patients who have Alzheimer.

Memantine hydrochloride is the common name of 1-amino-3,4-dimethyladamatane HCl approved by the FDA as a drug for treating the Alzheimer disease with neuroprotective activity.

Memantine is water soluble and has a characteristic intense bitter taste, which is very difficult to mask. It is available commercially, under different brands, in the form of tablets, tablets with prolonged action and in solution to be administered in drops.

J. Hernández Martín et al (Farm. Hosp. 2013: 37 (3): 198-208) in their article "Adaptación de la guía farmacoterapéutica de un hospital socio-sanitario a pacientes con disfagia" (*Adapting the pharmacotherapy guide in a social-sanitary hospital to patients with dysphagia*) recommend grinding the tablets and adding the powder formed to jellies or foodstuff for administration and they suggest, particularly with respect to memantine, using a solution (10 mg/ml) mixed with puree, compote or cream to aid swallowing.

For those skilled in the art, the prior grinding of tablets is not an optimum alternative for administering, because of how it destroys the pharmaceutical characteristics and properties of the original composition. Commercial tablets exist containing immediately released memantine and tablets with prolonged release and in both cases the grinding can significantly affect the properties of the original composition.

Also, the simple grinding or crushing of tablets and the adding of water leads to the presence of agglomerates or particles generally of a significant size which are uncomfortable in the buccal cavity.

During 2006 (International Journal of Pharmaceutical Compounding Vol. 10, No 4; 316-317) a description was given of the stability of memantine in an extemporaneous liquid preparation made by crushing tablets and subsequently suspending them in water, simulating the tablet grinding possibilities available in hospitals, clinics and in the homes of patients (who due to swallowing problems cannot swallow whole tablets). The result of this study revealed that the extemporaneous oral preparation made up of memantine and water is stable at room temperature only for 7 days, and during this time a variation occurs in the original concentration, over 10%, which leads to the formation of aggregates front the components of non-water soluble tablets, due to the absence of suspension agents. The formation and presence, in the buccal cavity of said non-water soluble precipitates or aggregates do not facilitate the swallowing of the extemporaneous preparation prepared by the simple grinding applied frequently in some hospitals, clinics or patients' homes. The authors do not mention the size of the particles that are formed with said grinding or the influence that the particle size has on swallowing by patients with dysphagia.

Patent Application US 2010/0215740 (Rubicon Research Private Limited) describes oral disintegrating tables containing memantine with the taste masked by different procedures, which disintegrate in the buccal cavity, preferably in 60 seconds according to that indicated in "the field of the invention" and in even less time to the order of 25 to 30, 20 to 30, 40 to 55, 30 to 45 seconds as highlighted in Examples 1, 2, 3 and 4. Although the tablets described represent an advance for treating patients with Alzheimer as opposed to the traditional oral tablets, the presence of the tablets in the buccal cavity until they disintegrate completely, 20 to 45 seconds, is not a practical or definitive solution for patients who, apart from suffering from Alzheimer, also have dysphagia. Neither does it mention whether the particles resulting from the disintegration of the tablets, which are also present in the buccal cavity, are uncomfortable or not.

Patent Application US 2015/023443 A1 (Aug. 27, 2015), a partial continuation of application US 2011/0046232 A1 (Forest Laboratories, Feb. 24, 2011), describes two different pharmaceutical compositions containing memantine with the taste masked previously using various procedures. These are film-type compositions or orally dissolving tablets. Both compositions offer the patient a superior alternative to swallowing traditional oral tablets also containing memantine, particularly because they reduce the bitter taste of the memantine content.

However, they have the following limitations:
i) Example 4) indicates that the disintegration time is approximately 24 seconds (according to USP assay (compared with a similar assessment, the tablets described in this invention have a disintegration time of only 5 seconds))
The presence in the buccal cavity of a tablet that is disintegrating during the mentioned time bracket is uncomfortable for every normal individual and is a significant hindrance for all patients with neurological problems or dysphagia.
ii) The document also mentions the particle size distribution of the granulate formed by the composition with the masked taste (Example 2—Table 4). As described; approximately 30% of the masked particles have a size of 0.5 MM (500 microns) 47% have a size of 0.297 MM (297 microns), 8% have a size of 0.250 MM (250 microns), 9% has a size of 0177 MM (177 microns) and the rest are a smaller size. It is important to highlight that the large size particles mentioned are not convenient because once the tablet has disintegrated in the buccal cavity, said particles may be chewed involuntarily before swallowing and consequently the coating that masks the bitter taste of the memantine contained, is destroyed.

It is important to highlight that the presence in the buccal cavity of a tablet that is disintegrating for approximately 30 seconds is uncomfortable for all normal individuals and is a significant hindrance for all patients with neurological problems and dysphagia. Consequently, the oral disintegrating tablets described in both patents are not a useful alternative for patients with dysphagia.

The presence of pharmaceutical compositions in the form of drops offers another option with a view to the dysphagia that is so frequent among patients with Alzheimer. It allows administering memantine in solution on its own or mixed with foodstuffs as indicated by J. Hernández Martin and collaborators in their previously mentioned article.

However memantine in solution has an intense, prolonged bitter taste that leads to the product being rejected or not accepted by the patient, and requires masking the bitter taste with jellies or foodstuffs with a pleasant taste. Otherwise, its acceptance by patients is minimum or zero.

Consequently, to date no pharmaceutical composition containing memantine has been described with the following advantages and properties:
a) it has a pleasant taste
b) it does not leave uncomfortable residue in the buccal cavity
c) the composition is easy for the patient to swallow
d) that the composition also offers a flexible posology. That is, that the same composition is satisfactory for starting the treatment with the lower dose and allows increasing the posology to the maximum or maintenance dose as doctors usually advice their patients with Alzheimer. Generally, it is recommended to start the treatment with 5 mg/day during the first week, raise it to 10 mg/day for the second week to 15 mg/day for the third week, and to 20 mg/day for the fourth week of the treatment, or other posology sequences, but in all cases with successive, regular increases. Consequently, the flexible posology of the pharmaceutical composition is a practical aspect that deserves special consideration, and which is absent in commercially available oral tablets.
e) that the composition can be administered to special patients using an enteral feeding tube like their usual food.

Where each and every one f the aspects described are of practical interest for satisfactorily administering and continuing the treatment in patients with neurological problems and dysphagia.

SUMMARY OF THE INVENTION

The aim of the invention is a premixture of a memantine pharmaceutical composition for oral administration characterized as indicated in claim 1. The subordinate claims indicate alternatives or optional improvements to the premixture according to the invention.

Another aim of the invention is a memantine pharmaceutical composition for oral administration characterized in that it comprises a premixture according to the invention. The subordinate claims indicate alternatives or optional improvements to the premixture according to the invention.

A further aim of the invention are procedures for preparing the premixture and the composition according to the invention, characterized as indicated in the corresponding independent claims. In each case, the corresponding subordinate claims indicate alternatives or optional improvements to the procedures according to the invention.

This invention resolves ail the above-mentioned aspects that are of practical interest to patients, with one single, pharmaceutical composition.

The composition is administered to the patient in the form of oral suspension, without the bitter taste of memantine mentioned and with very small size memantine-containing particles (90% with an average diameter less than 170 microns) which facilitates a patient's normal swallowing.

The pharmaceutical composition is prepared from an innovative premixture which is characterized by:
   a) the small size of its memantine-containing particles
   b) the suspension of the premixture in water has a pleasant taste
   c) and it does not form uncomfortable aggregates m the buccal cavity Based on the commonly used premixture, the chosen composition is made and it is available in various forms, including as follows:
   a) as a suspension.
   b) as a powder for preparing the suspension in water or any other drink before administering it; and
   c) as oral disintegrating tablets (our, which can also be mono- or multi-grooved) to form the suspension with water also prior to administering. Said tablets, thanks to their fast disintegration in contact with the buccal saliva, permit being administered directly to the patient since the oral suspension with the saliva starts to form within 10 seconds, creating a complete suspension within 15 seconds which has a pleasant taste without any annoying particles. This provides an additional alternative to supplying the composition according to the invention to the patient.

All these forms are suitable for being present in the buccal cavity as a the suspension containing the particles with memantine. Also, all the composition are divisible and contribute to a flexible posology that each patient under medical indication requires.

All of them, as suspensions comprise the advantages and properties indicated above.

The pharmaceutical composition in this invention, in the form of a suspension, contains preferably between 1 to 3 mg/ml of memantine and preferably 2.5 milligrams per millilitre and has no uncomfortable lumps or aggregates in the buccal cavity.

The oral disintegrating tablets (ODT) that have an in vitro disintegrating time according to USP assay, of only 5 seconds, and which start to disintegrate in the but cavity within 10 seconds forming a suspension with the saliva, and unexpectedly reveal a total disintegration time in the buccal cavity under 15 seconds, also revealed that they can be administered directly to the patient and without the need to administer water simultaneously to facilitate swallowing.

The Cochrane Library, 2009 (Issue 2 Art no CD007209 Chichester, UK, John Wiley & Sons Ltd.) mentions that the use of enteral feeding is frequent among patients with advanced dementia who have poor nutritional intake. The authors highlight that in a survey conducted in USA by Mitchell St. and others (JAMA Jul. 2, 2003—290 (1):73-80) 34% of 186,835 residents in centers for geriatric patients with advanced cognitive impairment were tube-fed. Nutr. Hosp. 2006:21 (Supl. 4), 3-4 mentions that the difficulty in swallowing of some patients is so significant that enteral feeding through a tube is the most convenient, practical alternative for feeding and administering medicines. Also that the higher survival age of the population, the developments in enteral feeding and the tube fitting techniques have facilitated the diffusion of this type of feeding and medicine administering using enteral tubes, and they help to resolve the specific need of many patients. In the particular case of medicines, it is highlighted that the tube becoming blocked with the medicine is a frequent practical complication. Grinding the tablets as it is done in hospitals and homes and suspension in water are not optimum alternatives in all cases. Frequently the tube becomes blocked by the size of the particles resulting from said grinding process.

Unexpectedly, the suspension prepared from the composition that is mentioned in this invention and described in the Experimental Procedure proved to be an innovative alternative, not mentioned previously for administering memantine through an enteral tube and only feasible by the small size of the memantine-containing particles in suspension.

In the compositions prepared with the premixture according to the invention the maximum average size of the particles is 170 microns (for 90% of the particles) in the case of a suspension formed by disintegrating in water the fast disintegrating tablets, and it is even less in the case of a suspension or in the case of a suspension that is formed from the powder for suspension by adding water or another drink. The particles do not obstruct the enteral feeding tubes and also allow memantine to be administered via this channel to patients with severe dysphagia. A particle size that is not obtained by the simple grinding of memantine-containing tablets in hospitals or homes.

The invention describes in the Experimental Procedure the procedure for preparing the specific commonly use premixture and subsequently preparation using the said premixture of the pharmaceutical composition with a pleasant taste and small memantine-containing particles.

For patients with Alzheimer who also have diabetes, a preparation is described for a sugar-free composition.

DESCRIPTION OF THE FIGURES

Included are microphotographs of suspensions in water containing particles with memantine according to this invention and of the suspension in water of commercially available oral tablets, ground in advance, according to the usual practice of administering oral tablets to patients with dysphagia.

The preparation of the composition for administering to the patient in the form of a suspension is described in the corresponding examples.

The microphotographs were taken using a Nikon Coolpix 4500 camera and Leitz Wetzler Optical Microscope. The magnification used was 100× and the observation took place in a wet medium.

DETAILED DESCRIPTION OF SOME FORMS OF EMBODIMENT OF THE INVENTION

Premixture

The first aim of this invention comprises having a premixture that is completely free of the bitter taste of memantine which, when located directly in the buccal cavity, quickly forms a suspension with the saliva, which contains small size particles that do not alter normal swallowing. In other words, that the aggregates that the dry premixture forms naturally, have the particular characteristic of disintegrating with the saliva in a few seconds, and therefore are not uncomfortable in the buccal cavity and facilitate swallowing. This premixture makes it possible to prepare a composition according to the invention.

The innovative, commonly used premixture is obtained through two stages that include the following operations:

a) Preparing Pellets Containing Memantine with a Partially Masked Taste

On to a mixture of powders made up of microcrystalline cellulose (Avicel PH 200), pregelatinised starch and silicon dioxide (Aerosil 200), in a fluid bed and by top spraying at a temperature less than 50° C. a homogenous suspension in water-ethanol is added, containing memantine previously dissolved in the mixture of solvents together with corn starch and polyethylene glycol.

Subsequently a suspension is applied with 20% polyvinylpyrrolidone in water and finally it is coated with a suspension in isopropyl alcohol-water containing the cationic copolymer of dimethylaminoethyl methacrylate, butyl methacrylate and methyl methacrylate (preferably Eudragit EPO) and magnesium stearate by tangential spraying and at a product temperature of between 25 and 30° C.

The pellets obtained partially keep the bitter taste of the memantine.

The innovative prior dissolving of memantine in water-ethanol provides the following advantages:
  i) it aids the even distribution of memantine over all the particles in the mixture
  ii) it eliminates the presence of crystalline and more concentrated memantine over some particles in the mixture. This drawback occurs with a physical mixture containing memantine in a solid or crystalline form
  iii) applying the previously dissolved memantine over the whole mass improves the uniformity of contents of the pharmaceutical composition to be prepared.

However, even with the advantages offered by an even distribution of the previously dissolved memantine, the masking of the taste with the cationic copolymer of dimethylaminoethyl methacrylate, butyl methacrylate and methyl methacrylate (Eudragit EPO type) in the percentage applied, was partial and the pellets obtained partially kept the bitter taste of memantine.

The Eudragit EPO copolymer is known to maintain the coating produced at pH 5.0 or higher in the buccal cavity and it is useful for masking tastes and is lost at the acid pH from the stomach.

Under experiment conditions it was observed that said coating was not uniform on all the particles containing memantine on their surface, and the pellets obtained partially kept the characteristic bitter taste of memantine.

The possibility of increasing the percentage of Eudragit EPO to ensure total masking of the bitter taste was discarded immediately, because it would cause a reduction in the concentration of memantine in the mass and a longer release time for the active ingredient memantine in the acid pH of the stomach, where the active ingredient is absorbed.

b) Preparing the Premixture Without the Bitter Taste, Which is Commonly Used and has a Pleasant Taste With the pellets obtained in the previous stage (a) which have a slight bitter taste, together with an even mixture of powders made up of sucralose, peppermint essence and lemon essence, an even mass was formed mixing the whole ensemble for no less than 30 minutes and preferably 60 minutes.

The presence of sucralose in solid form in the mixture surprisingly determined the complete absence of the bitter taste from the memantine, masked partially by Eudragit EPO. In a way not previously envisaged, sucralose even added in solid form revealed an excellent dissolving speed in buccal saliva, simultaneously adding its high sweetening power to the buccal cavity and neutralising the bitter taste remaining from the memantine contained in the pellets. It is known that sucralose does not alter the glucose levels in the blood. Its presence adds a sweetening capacity and it is not counter-indicated for diabetic patients. Federal Register: 21 CFR Part 172, Docket No. 87 F-0086, Apr. 2, 1998 indicates that only between 11 to 27% of the sucralose swallowed is absorbed and the rest is eliminated in faeces, and the fraction absorbed in eliminated in urine.

Also surprisingly it was observed that simultaneously adding the peppermint and lemon essences gave the premixture a pleasant taste, which helped the composition it contains to be swallowed easily.

The components mentioned (sucralose and essences) led to a premixture not described to date, which contains memantine with its bitter taste fully masked and where the premixture has a particularly pleasant taste. Precisely because of the essences it contains, and the sucralose.

Thanks to the innovative use of sucralose and the essences as mentioned it was possible to discard using a greater percentage of copolymer to fully mask the bitter taste of memantine in the pellets. An increase in the copolymer content would simultaneously increase the release time of the active ingredient in the acid pH of the stomach, and it would negatively affect the release time of the active ingredient in the pharmaceutical form that is prepared subsequently.

The unexpected full masking of the bitter taste of memantine using sucralose and the selected essences also has the following practical advantages:
  a) the sucralose and the essences were added to the granulate with the partially bitter tasting pellets using a simple physical mixture without any technological complexity.
  b) the presence of sucralose and essences does not affect the release speed of memantine in the stomach pH,
  c) the premixture obtained has not bitter memantine taste, and instead has a pleasant taste.

The premixture obtained had the following characteristics:
  1) it was added to the buccal cavity of volunteers;
  a) a few seconds after being added it created a suspension with a pleasant taste and free of uncomfortable particles or aggregates.
  b) it was observed that the suspension formed between the premixture and the saliva was easy to swallow,
  2) in the in vitro assay and when determining the particle size using Laser Diffraction it was observed:
    That the dry premixture suspended in water initially formed aggregates or lumps which, when shaken gently or subjected to ultrasound, quickly disintegrated and led to a suspension containing 90% of particles with a size smaller than 77 microns.

The premixture, due to its characteristics and easy swallowing, proved to be useful in the preparation of pharmaceutical compositions to be administering orally to patients in the form of suspension, where the suspension to be administered is pemmican, or prepared prior to administering. So for example, single or multiple dose suspensions prepared industrially and in conditions to be administered, and, also single or multiple dose suspensions prepared prior to administering by adding water or other drinks.

Tablets

Another aim of this invention is to prepare quickly disintegrating tablets with the above-mentioned premixture, to form the suspension mentioned with water prior to administering or by directly placing the tablet in the buccal cavity.

As indicated in greater detail in the Experimental Procedure by adding to the commonly used premixture a coprocessed product made up of mannitol, starch, sodium croscarmellose, colloidal silica and silica (Pharmabust 500®), cross-linked povidone and finally sodium stearyl fumarate made it possible to obtain a mixture of powders which with simple direct compression produced grooved tablets that disintegrate quickly in the to presence of water of saliva.

The grooved tablets revealed:
 a) that they have an in vitro disintegrating time according to the assay described in USP 32 of just 5 seconds. When the tablet is placed in the buccal cavity it starts to disintegrate within 8 seconds and it fully disintegrated within 15 seconds.
 b) that the suspension formed by the grooved tablets in a small volume of water prior to administering, or, when placed directly in the buccal cavity, has in both cases a pleasant taste and the suspension is free of particles or aggregates that are uncomfortable for the buccal cavity. These characteristics determine its easy swallowing.
 c) in volunteers it was confirmed that said quickly disintegrating tablets offer practical possibilities for administering to patients and they are free to choose. These possibilities were:
  first disintegrating in a small volume of water and administering the suspension formed.
  first disintegrating in water and adding the suspension formed to food,
  first disintegrating in water and administering the suspension formed by enteral feeding tube, for example: type K108;
  and optionally by directly placing in the buccal cavity without the need to administer water and where with the existing saliva the easy to swallow suspension is quickly formed,
 d) that they are easily divisible by their groove and allow adapting the posology of memantine to the patient's need.

The alternatives for administering to patients offered by the tables mentioned are practical and innovative, and have not been described by other oral memantine-containing tablets, and are only, feasible thanks to their disintegration speed and flavour, Industrially, preparing grooved, oral disintegrating tablets, also known by the initials ODT, from the commonly used premixture is simpler and more economical than the preparation described in the bibliography for ODT tables with other active ingredients and technologies Flashtab, Wowtab, Orasolv, or others. They all require complex equipment and facilities.

The tablets that are prepared with the premixture mentioned have a greater disintegrating speed than that recommended by the regulating authorities such as the Food and Drug Administration in USA, which defines that the ODT tablets must have an in vitro disintegrating, time of approximately 30 seconds, or the European Pharmacopeia which highlights that orodispersible pharmaceutical formats must have a disintegrating time under 360 seconds. These times are long enough to be uncomfortable for any individual and much more so for patients with. Alzheimer who have dysphagia.

Powder for Suspension

Another aim of this invention is the preparation of powder to form a suspension with water or another drink prior to administering to the patient.

In this case by adding microcrystalline cellulose (Avicel Cl 611), sucralose essences and sugar to the premixture described, as explained in the Experimental Procedure, a final mixture of powders was obtained.

Subsequently the final mixture was conditioned into single-dose units in aluminium/aluminium sachets, or, in phials for the extemporaneous preparation of the multi-dose suspension by simply adding water and shaking prior to administering to the patient.

For patients with Alzheimer and diabetics, a final mixture was also prepared that was conditioned in a similar way but without sugar.

The suspension formed by adding water to the single-dose sachets revealed, through Laser Diffraction, that 50% of the particles in suspension have a diameter of 60 microns and 90% are under 120 microns.

In volunteers it was revealed that it has a pleasant taste, is free of uncomfortable particles or aggregates in the buccal cavity, and is surprisingly easy to administer to the patient.

Suspension

Another aim of this invention is the preparation of a permanent and multi-dose suspension from the premixture according to the invention, as described in the Experimental Procedure, which contains in a non-limiting way between 1 mg and 3 mg of memantine per millilitre of suspension, has a pleasant taste and is also easy to swallow.

Laser Diffraction revealed that the permanent suspension has 50% of particles with an average diameter of 50 microns and 90% of particles less than 110 microns.

The permanent suspension offers flexible posology by allowing the posology to be adapted to the specific needs of the patient. For example, starting with the initial recommended dose of 5 mg/day up to the 20 mg/day with the same product.

The permanent suspension was also prepared for patients with Alzheimer who have diabetes. In this case, without sugar, the sucralose content can be increased if desired.

The suspension and the compositions mentioned above in each case allow administering memantine contained in particles in the form of an oral suspension that is easy to swallow thanks to the absence of the bitter taste of memantine, the pleasant taste of the suspension and the small size of the particles in suspension.

Administering Memantine in Suspension Through an Enteral Feeding Tube

Another aim of this invention is to administer memantine in suspension through an enteral feeding tube.

Unexpectedly the suspension for administering that is described, revealed a new alternative for administering memantine through an enteral feeding tube, as a direct consequence of the small size of all the particles containing memantine. In all the formats for administering memantine in suspension described, it was revealed that the average diameter of the particles in less than 170 microns, a size that is not obtained by simply grinding in hospitals or homes from oral memantine-containing tablets. This particle size is present both in the pre-prepared suspension and in the powder for forming the suspension by adding water, and also in the suspension for administering, which comes from disintegrating the quickly disintegrating tablets in water.

In a non-limiting fashion, the following examples described in the Experimental Procedure illustrate the way of implementing this invention.

EXPERIMENTAL PROCEDURE

Example I

Commonly Used Premixture to the Chosen Pharmaceutical Composition

The premixture was prepared according to the following sequence of stages and operations:
Stage I: Preparing Pellets Containing Memantine with a Partially Masked Bitter Taste.
The sequence was:
a) Mix in cubic mixer.

| | | |
|---|---|---|
| Aerosil 200 (silicon dioxide) | 8 grams | (1.0% w/w) |
| Pregelatinised starch | 68 grams | (8.5% w/w) |
| Avicel PH 200 (microcrystalline cellulose) | 724 grams | (90.5% w/w) | at 25 rpm for no less than 10 minutes.
Where:
50% of the AVICEL PH 200 particles were larger than 150 microns
2) the Aerosil 200 particle size was 7 to 16 microns, but it can form aggregates of 10 to 200 microns
3) the pregelatinised starch particle sizes distribution was between 30 and 150 microns
   b) Preparing in parallel a suspension containing:

| | | |
|---|---|---|
| Water | 1450 grams | (57.2% w/w) |
| Ethanol | 621.5 grams | (24.5% w/w) |
| Memantine | 229.1 grams | (9.0% w/w) |
| Pregelatinised corn starch | 152.13 grams | (6.0% w/w) |
| Polyethylene glycol 6000 | 83.7 grams | (3.3% w/w) | dissolving the memantine all the solvent formed with water-ethanol, successively adding the polyethylene glycol and pregelatinised starch under stirring for no less than 1 hour and until an even suspension is obtained.
   c) Granulating the powder mixture in a Chongqing DLP ⅗ fluid bed by top spraying a) with the suspension
   b) keeping the suspension stirred throughout the process and with a temperature of the powder mixture under 50° C.
   d) Coating in a fluid bed above mixture c) by top spraying with a suspension containing 20% polyvinylpymilidone (PIP K 30) in water and obtaining a first granulate containing memantine.
   e) Preparing second suspension for coating made up of:

| | | |
|---|---|---|
| Isopropyl alcohol | 2227 grams | (83.73% w/w) |
| Water | 116.23 grams | (4.37% w/w) |
| Eudragit EPO | 275.28 grams | (10.35% w/w) |
| Magnesium stearate | 41.22 grams | (1.55% w/w) | and coating 1266 grams of the above pellets d) in a fluid bed by bottom spraying (also called Wurster system) or tangential spraying at a product temperature between 25 and 30° C. 1550 grams of pellets were obtained.
The pellets obtained had the following characteristics:
   a) Memantine taste, partially masked but, a slight bitter taste is noticeable in them.
   b) The memantine content was 13.3%
Through 3 successive operations with the same procedure described, it was shown that the memantine content in the pellets with a partially masked taste was between 12.0 and 14.6%.

Stage II: Forming with the Above Pellets a Premixture Free of the Bitter Taste of Memantine, with a Pleasant Taste and Commonly Used to Prepare the Chosen Pharmaceutical Composition.
Specifically:
a) After passing through a sieve with a mesh size a 710 microns the following were added and mixed in the cubic mixer for 10 minutes:

| | | |
|---|---|---|
| Sucralose | 66.85 grams | (5.21% w/w) |
| Peppermint essence | 74.88 grams | (5.84% w/w) |
| Lemon essence | 140.39 grams | (11% w/w) | b) The mixture obtained was added together with 1000 grams of granulate with partially masked taste prepared according to Stage 1 above, to the mixer. They were mixed for 30 minutes.

Obtained: 1282.1 grams c) Sieving with a mesh size of 710 and discarding aggregates.

The Premixture Obtained had the Following Characteristics:

a) Substantial absence of the bitter taste of the memantine it contains and the presence of a gentle, pleasant taste corresponding to the essences it contains.

b) The memantine content was 10.4%.

c) A total of 0.9 grams of premixture were suspended in 10 ml of water using Laser Diffraction in Malvern Mastersizer 2000 equipment under the following conditions: Pump/Stir, speed; 2800 p.m., Refraction Index: IR Standard 0.01, IR Purified Water: 1.33; Analysis Model: general purpose, Obscuration: 15.0-20.0%; Sample stabilising time: 1 minute and Duration of the measurement: 5 seconds, and considering that D (0.90) means the particle size under which 90% of the sample was included, it was observed:

i. That 90% of the aggregates of particles that are formed by suspension in water have a size less than 1454 microns (D (0.90)=1454 microns).

ii. But by simply stirring or applying ultrasound before for 1 minute, the particles in the above suspension are broken down and it is confirmed that 90% of the particles in the premixture are less than 77 microns (D 0.90=76.9 microns). A size that is not uncomfortable in the buccal cavity. Surprisingly, even starting with original ingredients like raw materials with a particle size larger than 150 microns, an end product is obtained, the premixture where 90% of the particles are under 77 microns; this final result is an unexpected consequence of the procedure (mixing, granulating in the presence of water-ethanol-coating with aqueous PVP suspension, etc.) and not the size of the particles of the original excipients.

d) Surprisingly, when the premixture is placed in the buccal cavity of volunteers, the suspension that forms with the saliva disintegrates immediately and no uncomfortable particles remain in the buccal cavity.

e) Dissolving Assays:

1) In the Buccal Cavity and Medium Similar to Saliva.

The disintegration of the aggregates of particles in the premixture in contact with water stirring or with saliva is immediate this is an innovative and unforeseen characteristic which, together with the full masking of the unpleasant taste of memantine, the pleasant taste and the small size of the particles, means that the compositions described are easy to prepare.

According to the bibliography the pH of saliva is between 5.4 and 6.1 in base conditions, reaching up to 7.8 through stimulation (Kalaritzi et al Pharm. Res, 23(19 (2006) (613-617) and the volume of saliva present in the buccal cavity is less than 2.0 ml. (F. Lagerlof et al, J. DENT. RES. 63 (5) (1984); 618-621) even when daily saliva production is over 1000 ml.

There is no uniform criterion in the bibliography to determine the amount of active ingredient that is dissolved in the buccal cavity. The analysis techniques described in the bibliography for determining the solubility of active ingredients in conditions similar to saliva, use much larger volumes than the volume of saliva present in the buccal cavity. So for example, a dissolving volume is mentioned of between 100 and 900 ml. The results are naturally a guideline and useful even when the percentage of dissolution determined by such procedures is higher than the dissolution that takes places in the small volume of saliva present in the buccal cavity.

In our case we followed the conditions mentioned in the Japanese Pharmacopea XV, Dissolution Medium No. 2, pH 6.8; 500 ml at 50 rpm.

Surprisingly the premixture revealed:

After 15 seconds: absence of dissolved memantine

After 30 seconds only 5% of the memantine present in the premixture dissolved and After 60 seconds only 14% dissolved.

The determinations were only carried out up to 60 seconds, the maximum time that can be considered reasonable for the presence of a suspension in the buccal cavity without involuntarily swallowing it.

The analysis results obtained in vitro were clearly compatible with the assays that revealed in volunteers the absence of the taste of the premixture placed in the buccal cavity.

2) Dissolving Memantine in the Premixture at Gastric pH

This was carried out under the following conditions: 900 ml medium of simulated gastric fluid (0.1 N of hydrochloric acid with sodium chloride (solution in water at 2%); blade at 75 rpm (according to USP 38).

The results revealed a high memantine release speed from the premixture reaching 94% in just 15 minutes. A much higher value than that established by USP 38 for memantine oral disintegating tablets, for which it establishes that the composition must release at least 80% of the memantine it contains after 45 minutes.

Both determinations for dissolving the memantine present in the premixture, not described previously in the art, ensure the absence of any unpleasant taste in the buccal cavity and the immediate release of memantine into the stomach medium.

The absence of the unpleasant taste of memantine and the small average size of the particles containing it, determine in a way not previously foreseen, the possibility of using the premixture described in the preparation of pharmaceutical compositions to he administered to patients in the form of a suspension. In a non-limiting way as a suspension, or, as a suspension prepared prior to administering. And including, applying the premixture thanks to its favourable characteristics to preparing quickly disintegrating tablets that form the suspension in a few seconds with the saliva in the buccal cavity.

Example II

Using the Pellets Obtained in Stage I of Example I, the Following Premixtures were Prepared Without the Bitter Taste Memantine, with a Pleasant Taste and Commonly Used to Prepare the Chosen Pharmaceutical Composition by Following the Technique in Stage II of Example I.

Specifically:

a) After passing through a sieve with a mesh size of 710 microns, sucralose and the following essences were added and mixed in a cubic mixer for 10 minutes:

|  | IIA | IIB | IIC | IID | IIE | IIF |
|---|---|---|---|---|---|---|
| Sucralose | 66.85 g. | 66.85 g. | 66.85 g. | 66.85 g. | 66.85 g. | 66.85 g. |
| Peppermint essence | 74.88 g | | | | | |
| Lemon essence | 140.39 g | | | | | |
| Cherry essence | | 140.50 g | | | | |
| Raspberry essence | | | 140.50 g | | | |
| Fruity essence | | | | 140.50 g | | |
| Grapefruit essence | | | | | 140.50 g | |
| Lime-lemon essence | | | | | | 140.50 g |
| Total Weight of the Premixture | 1282.1 g | 1207.3 g | 1207.3 g | 1207.3 g | 1207.3 g | 1207.3 g | b) The mixture obtained was added together with 1000 grams of granulate with a partially masked taste prepared according to Stage I above, to the mixer. They were mixed for 30 minutes.
c) Sieving through a 710 mesh size and discarding aggregates.

All the premixtures obtained with the various essences revealed:
a) Absence of the characteristic bitter taste of the memantine they contain
b) Located in the buccal cavity of volunteers they quickly formed a suspension with the saliva, without uncomfortable particles in the buccal cavity and with a pleasant taste.

Example III

Grooved Tablets that Disintegrate Quickly in Water to Form a Suspension that is Easy to Administer Orally or by K-180 Type Enteral Feeding Tube The tablets thanks to their fast disintegration and the suspension they form with the saliva in the buccal cavity can also, optionally, be administered directly.

They were prepared according to the following sequence:
To 95.89 grams (38.36% w/w) of the premixture obtained according to Example I above, after passing through a sieve with a mesh size of 710 microns, the following, were added in a cubic mixer.
133.7 grams of Pharmabursth® 500 (53.48% w/w)
15.0 grams of cross-linked povidone (Kollidon CD) (6.0% w/w)
0.4 grams of peppermint essence (1.76% w/w)
and they were mixed for 15 minutes.

Where the excipient called Pharmabursth 500 corresponds to a mixture of commercially available SPI Pharma and made up of: mannitol, sorbitol, maltitol, crospovidone, copovidone and silicon dioxide and the chosen cross-linked povidone was Kollidon CD.

Subsequently, to the above mixture, 5.0 grams (2% w/w) of sodium stearyl fumarate (Pruv) were added, after sieving through a sieve with a mesh size of 250 microns, and they were mixed for 5 more minutes.

The final mixture obtained was compressed in a Piccola compressor using a rounded and grooved, 9 mm diameter punch, with an average weight of 250 mg.

A total of 990 tablets were obtained.
Characteristics:
a) Average weight: 250 mg (268.75-231.25).
b) Memantine content: 9.6 to 9.8 mg.
c) The in vitro disintegrating time according to the assay described in USP 32 was 5 seconds.
d) Using the same procedure described, tablets were prepared containing 5 mg of memantine and grooved tablets containing 20 mg of memantine.
e) Dissolving. Assays for dissolving the memantine contained in the oral disintegrating tablets (ODT)

The percentage of dissolution of memantine in media corresponding to the buccal cavity and gastric pH values was determined under the following conditions:
1) Dissolution at Buccal Cavity pH
The assay was carried out according to the Japanese Pharmacopea XV: Dissolution Medium No. 2; pH 6.8-500 ml, blades, 50 r.p.m.

Two assessments were made and the average percentage of both indicated that the dissolution of memantine occurred as follows:
0% after 15 seconds,
5% after 30 seconds, and
16% after 60 seconds.
2) Dissolution at Gastric pH
The assay was carried out according to USP 38: 900 ml simulated gastric fluid; pH 1.2; basket, 100 r.p.m.
Two assessments were made and the average percentage of both indicated that the dissolution of memantine occurred as follows:
95% after 15 minutes,
96% after 30 minutes, and
98% after 45 minutes.

CONCLUSIONS

1) The dissolution of the memantine from the tablets at a pH similar to the buccal cavity level is null or minimum, particularly when the volume of the dissolution medium (500 ml) used in the assay was much higher than the usual volume of saliva generally present in the buccal cavity (2 ml). The result is fully compatible with the assay in volunteers who confirmed the absence of the characteristic bitter taste when the tablets are placed in the buccal cavity and disintegrate.
2) The dissolution of memantine at a pH similar to the gastric level revealed a high dissolution speed (after 15 minutes 95%) contributing to the gastrointestinal absorption of the active ingredient and it is significantly higher than that indicated by USP with the same assay for these tablets that contain memantine (not less than 80% after 30 minutes).
f) In 10 volunteers the following was determined:
1) That the disintegrating time in the buccal cavity starts in under 10 seconds and total disintegration is under 15 seconds.
2) That the mixture resulting from the disintegration of the tablet in the buccal cavity lacks the bitter taste of the memantine it contains, and the suspension that forms has a pleasant taste.
3) That no uncomfortable particles or aggregates are formed in the buccal cavity after the tablets disintegrate.
4) That the suspension that forms in the buccal cavity by adding the quickly disintegrating tablet (ODT) is easy to swallow.
g) Ways of administering the grooved tablets. Surprisingly, the tablets obtained, administered to 10 volunteers, thanks to their fast disintegration, lack of uncomfortable residue in the buccal cavity and pleasant taste, allowed for different forms of administration. These were:
1) Disintegrating in a small volume of water (5 to 10 millilitres) and administering the suspension formed.
2) Disintegrating in a small volume of water and adding food.
3) By swallowing directly and without the need to take any water, as a consequence of the significant disintegrating speed in the buccal saliva and the absence of uncomfortable particles.

The small size of the particles present in the suspension that is formed by disintegrating the tablet in water, also made it possible to assess in vitro the possibility of administering the suspension through an enteral feeding tube. The suspension formed does not obstruct the tube.

h) Flexible posology of the grooved tablets. The grooved tablets (ODT) with 10 mg of memantine proved to be particularly useful for starting the treatment in patients and subsequently increasing the daily dose. So, for example: Starting the treatment with half a tablet a day (5 mg/day) and subsequently continuing respectively with a whole tablet (10 mg/day), one and a half tablets (15 mg/day) or 2 tablets (20 mg/day).

i) Clinical assay. Administering the quickly disintegrating tablets to 26 elderly patients allowed confirming the possibility of administering the tablets under original formats not previously described. Out of the 26 patients included in the assay, 12 started their treatment with the quickly disintegrating tablets (ODT) and the other 14 patients were on prior treatment with commercially available tablets that have a similar memantine content. The results were as follows:

1) In 5 patients who usually require feeding with an enteral tube, the tablets were disintegrated beforehand in 10 millilitres of water and gently stirred, and then administered through a K-108 type enteral feeding tube.

No tube obstruction was observed with any of the administrations to patients, including those patients with more than 30 days treatment. This is a direct consequence of the small size of the particles in suspension containing memantine.

A significant difference was observed with the suspension formed after grinding and the suspension in water of commercially available oral tablets that frequently caused an obstruction in the tubes and prevented administering through this channel.

2) The suspension formed by previously disintegrating the tablet in a small volume of water or fruit juice (10 to 20 millilitres) was administered to 14 patients. The results indicated that:

a) It was accepted very well by all patients as a consequence of the pleasant taste of the suspension, the small size of the particles it contains and the absence of uncomfortable aggregates in the buccal cavity.

b) No patient showed any signs of intolerance during the administering, c) Patients with swallowing disorders, benefitted significantly and this was noticed by patients and doctors.

d) in patients who usually receive their medication through nasogastric or nasoenteric tubes, the suspension formed from the tablets mentioned offered a new and simple alternative for the administering memantine orally.

Both forms and types of administration mentioned for the tablets that disintegrate quickly in water or drinks, proved to be innovative, simple and more convenient for administering memantine to patients with swallowing problems than commercially available oral tablets.

Example IV

Preparing Powder for Administering in the Form of a Suspension, After Adding Water or Other Drinks in Single-Dose Units After passing through a sieve with a mesh size of 710 microns, the following were added successively to a V type mixer.

510.4 grams of Avicel Cl 611 (87.70% w/w).
14.92 grams of sucralose (2.56% w/w).
11.20 grams of peppermint essence (1.92% w/w).
45.53 grams of Durarome lemon essence (7.82% w/w).
And they were mixed for 10 minutes at 25 r.p.m.

To the above mixture, 95.89 grams (14.14% w/w) of the premixture containing memantine was added, after passing through a sieve with a mesh size of 710 micron, and they were prepared according to the description in Example 1. They were mixed for 10 more minutes. Finally, 1822 grams (72.78% w/w) of sugar were added, maintaining the mixing speed for another 15 minutes.

Obtained: 2500 grams.

The prepared powder for suspension was conditioned in aluminium/aluminium sachets with an average weight of 2.5 grams and a memantine content of 10 mg per unit.

In a subsequent assay with a similar procedure, the mixture obtained was conditioned in single-dose phials with an equal content and weight with sufficient capacity for adding water and being stirred before being administered in the form of an oral suspension.

Characteristics:

The suspension formed by adding the contents of a sachet with 10 mg of memantine in 5 to 10 millilitres of water had a pleasant taste and no uncomfortable particles or aggregates in to the buccal cavity.

Two compartment sachets containing 10 and 20 mg of memantine were prepared using the same procedure.

Example V

Preparing Powder for Administering in the Form of a Suspension, After Adding Water and Without Sugar, Containing Memantine for Patients with Diabetes and Dysphagia, in Single or Multiple-Dose Units After passing each component through a sieve with a 710 micron mesh size, the components were added successively to the V type mixer.

510.4 grams of Avicel Cl 611 (87.70% w/w).
14.92 grams of sucralose (2.56% w/w).
11.20 grams of peppermint essence (1.92% w/w).
45.53 grams of Durarome lemon essence (7.82% w/w).
and they were mixed for 10 minutes at 25 r.p.m.

To the above mixture, after passing through a sieve with a mesh size of 710 microns, 95.89 grams (14.14% w/w) of the commonly used premixture containing memantine was added, and they were prepared according to the description in Example I. They were mixed for 10 more minutes.

Obtained: 678 grams.

The prepared powder for suspension was condition in small aluminium/aluminium sachets with an average weight of 678 milligrams and a memantine content of 10 mg per unit.

In a subsequent, similar assay, the powder obtained was conditioned in small aluminium/aluminium sachets with an average weight of 1.356 grams and a memantine content of 20 mg per unit.

In subsequent operations and with the powder obtained, packagings with 10 and 20 milligrams of memantine were prepared, conditioned in two compartment, aluminium/aluminium sachets. These two compartment packagings allow administering optionally 5 or 10 milligrams of memantine to the patient, or 10 or 20 milligrams according to the indicated treatment.

The absence of sugar means that the composition is recommendable for patients with Alzheimer and diabetes.

Example VI

Preparing a Permanent, Multi-Dose and Divisible Suspension Containing Memantine It was prepared according to the following sequence of operations:

To 2000 grams of powder for suspension, prepared according to Example III, 9.6 grams of methylparaben and 1.2 grams of propylparaben were added as preservation agents in the V type mixer at 25 r.p.m. for 10 minutes. The above mixture was divided and conditioned in 150 ml glass phials with an average contents of 25 grams of mixture per phial, and an average memantine content of 100 mg per unit. After adding 100 ml of water and stirring, the units appeared as follows:
  a) An even suspension formed with a pleasant taste.
  b) With 1 mg memantine content per ml of suspension.
  c) When the suspension is placed in the buccal cavity, no uncomfortable particles or aggregates were observed and it was easy to swallow.
  d) When kept in the fridge for 6 months the suspension remained stable and the memantine content was not altered, and neither was the suspension's suspendability modified or the pleasant taste.
  e) The suspension was easily divisible according to the indicated posology and with a memantine concentration of 1 milligram/millilitre.
  f) Using Laser Diffraction it was observed that the suspension had 50% of particles with an average diameter of 50 microns and 90% of particles with an average diameter less than 110 microns.

In subsequent operations and with a similar procedure suspensions were prepared containing between 1 and 3 milligrams per millilitre of memantine and preferably 2.5 milligrams per millilitre.

Example VII

Preparing a Permanent, Multi-Dose Suspension Containing Memantine and Without Sugar Preferably for Patients with Alzheimer and Diabetes To 284 grams of the premixture containing memantine, obtained in Example I, the following were added, after passing dough a sieve with a mesh size of 710 microns:
  510.4 grams of Avicel CL 611 (60.8% w/w)
  4.93 grams of sucralose (0.6% w/w)
  24.5 grams of Durarome type lemon essence (2.92% w/w)
  14.4 grams of methylparaben (0.16% w/w)
  1.8 grams de propylparaben (0.21% w/w)
And they were mixed for 15 minutes in a V type mixer at 25 r.p.m.

Finally, the above mixture was divided and conditioned in 175 ml glass phials with an average contents of 8.44 grams of mixture per phial and an average memantine content of 300 mg. After adding the sufficient amount for 120 ml of water and stirring, the units appeared as follows:
  a) An even suspension formed with a pleasant taste.
  b) With a memantine content of 2.5 mg per ml of suspension.
  c) When placed in the buccal cavity no uncomfortable particles are observed and it is easy to swallow.
  d) When kept in the fridge for 6 months the suspension remained stable and the memantine content was not altered, and neither was the suspension's suspendability modified or the pleasant taste.
  e) Thanks to the lack of sugar, the composition is suitable for diabetic patients.
  f) The suspension is easily divided according to the posology indicated in each case.

Example VIII

Behaviour of the Pharmaceutical Memantine Composition for Administering Orally in the Form of a Suspension and Size of the Particles in Contains that Help to Facilitate the Swallowing Thereof The following samples were prepared to compare the behaviour each suspension.

Sample I—Corresponding to grooved, oral disintegrating tablets. The tablets were prepared according to the description in. Example above, the tablet was placed in a glass beaker, 10 ml of water were added, it was stirred and the suspension formed.

Sample II—Corresponding to a multi-dose suspension containing 1 mg/ml of memantine. The permanent suspension was prepared according to Example V and it was used directly during the comparison with the other samples.

Sample III—Corresponding to a suspension in water prepared prior to administering or an extemporaneous suspension preparation. The powder for the suspension prepared extemporaneously was prepared according to Example III above. The contents of one single-dose unit was suspended in (10 ml) of water, forming the suspension.

Sample IV—Corresponding to commercially available oral tablets (Lucidex Brand—Laboratorios Bagó S. A.—batch AVPN) ground previously. The tablets were ground and suspended in water-following the process used frequently in homes and hospitals for administering tablets to patients with Alzheimer and with difficulty in swallowing.

Studies and Results

Microphotographs:

Microphotographs were taken of each suspension above (Samples I, II, III and IV) using a Nikon Coolpix 4500 camera and Leitz Wetzlar optical microscope. The magnification used was 100× and the observation took place in a wet medium.

Figure 1:
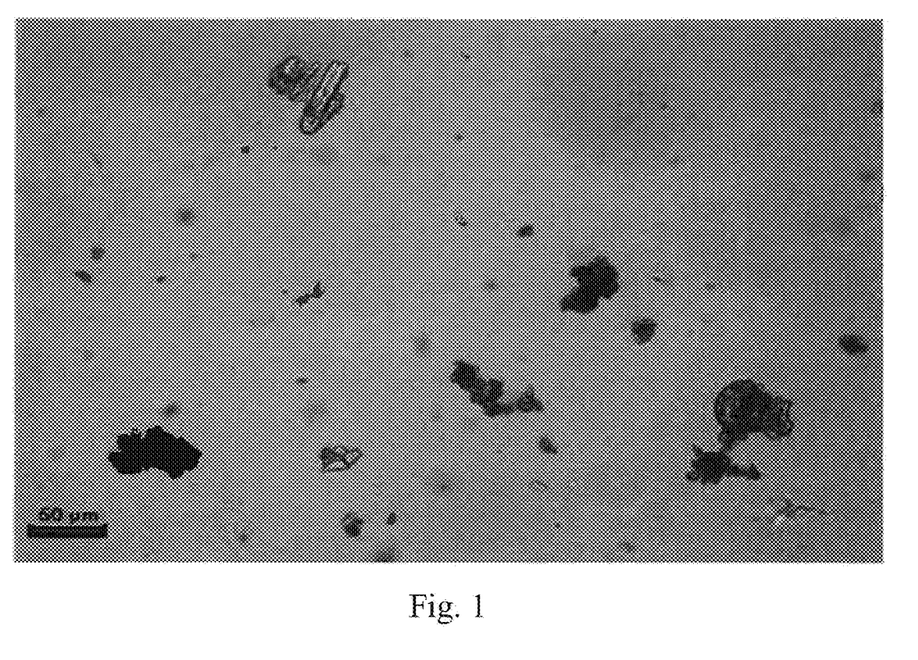
FIG. 1: Corresponds to a suspension formed by disintegrating oral disintegrating tablets (ODT) in water.
Figure 2:
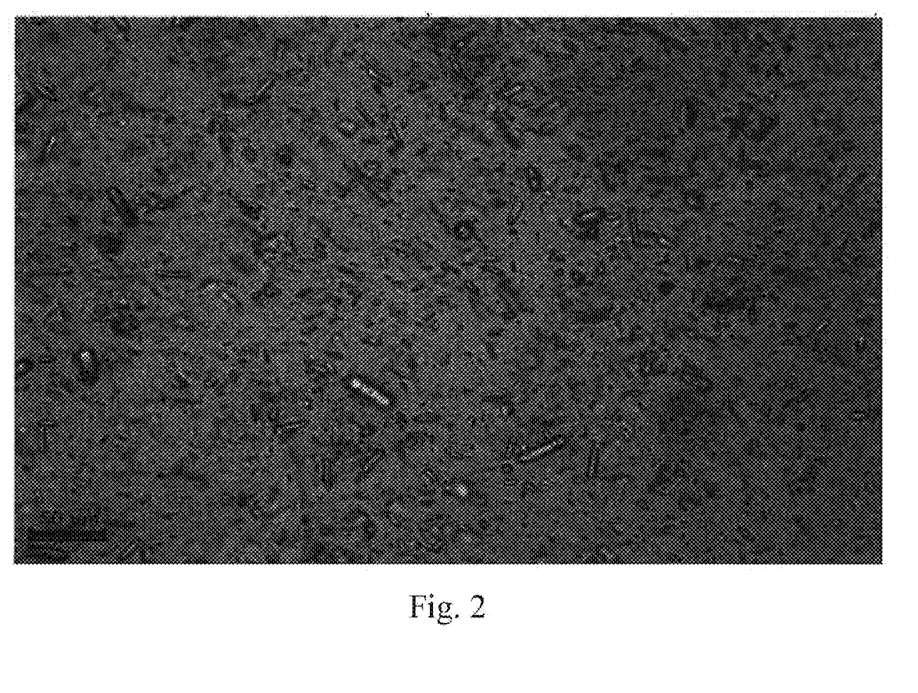
FIG. 2: Corresponds to a multi-dose suspension containing 1 mg/ml of memantine
Figure 3:
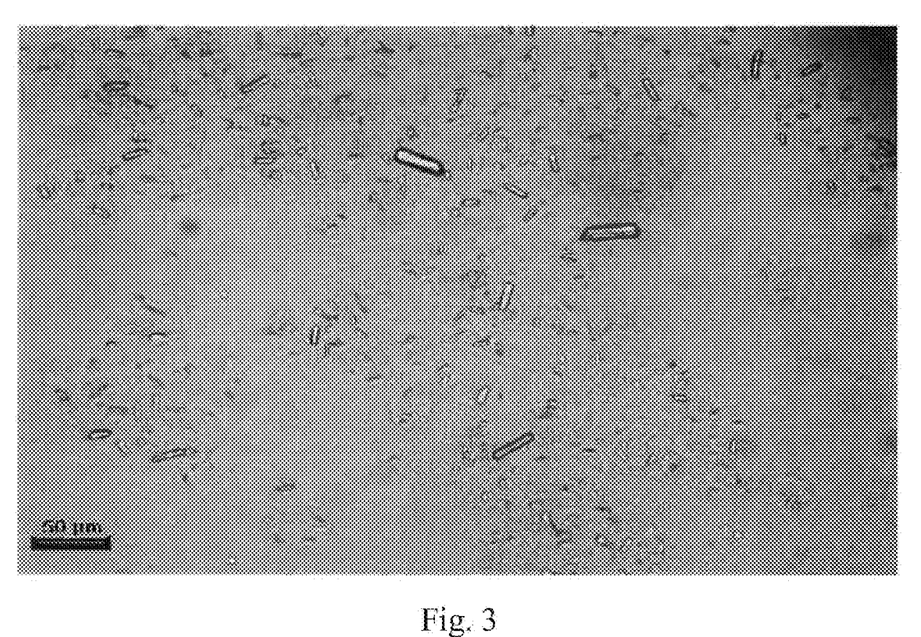
FIG. 3: Corresponds to the suspension prepared prior to administering or prepared extemporaneously.

In the microphotographs in FIGS. 1, 2 and 3 (corresponding to Samples I, II and III, respectively) it is observed that most of the particles have a size smaller than 50 microns and only some particles or aggregates have a size slightly larger than 50 microns.

Figure 4:
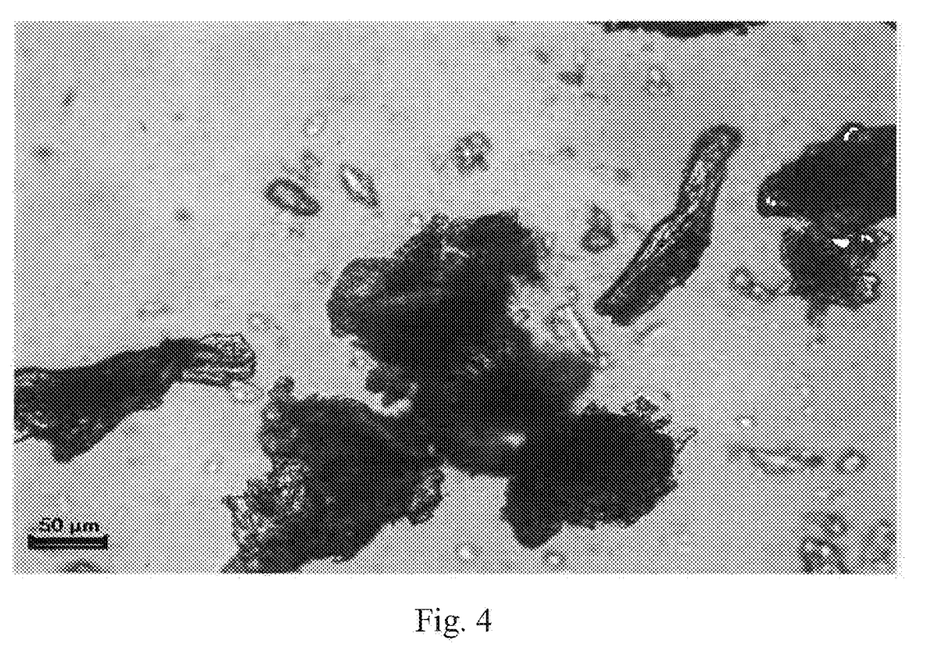
FIG. 4: Corresponds to the suspension in water formed with the powder resulting from grinding conventional oral tablets.

In the microphotograph in FIG. 4 (corresponding to Sample IV) it is observed that the in particle or aggregate size is notably higher than in the ones before. Most of the particles or aggregates arc irregular, have a size three or tour times larger with respect to the reference of 50 microns located in the lower part of the microphotograph. Only some isolated particles have a size smaller than 50 microns.

Distribution of Particle Size per Laser Diffraction

Malvern Mastersizer 2000 equipment was used under the following conditions:

Dispersing agent: water—Pump/Stir speed: 2800 rpm—Refraction index: IF Franhoufer, IR purified water: 1.33—Analysis Model: general purpose—Obscuration: 15.0-20.0%—Sample stablising time: 1 minute—Duration of the measurement; 5 seconds.

The results were as follows:

| SAMPLES | D (0.1) | D (0.5) | D (0.9) |
|---|---|---|---|
| I tablets | 11.454 | 50.516 | 147.090 |
| I Duplicate | 9.925 | 50.954 | 160.261 |
| II suspension | 17.494 | 44.732 | 93.703 |
| II Duplicate | 14.218 | 43.106 | 98.281 |
| III powder for suspension | 20.736 | 55.206 | 110.326 |
| III Duplicate | 23.420 | 54.845 | 105.475 |
| IV LUCIDEX ® | 17.850 | 94.214 | 211.624 |
| IV Duplicate | 16.898 | 93.954 | 217.182 |

For memantine in suspension (Samples I, II and III) the values of the D parameter (0.50) indicated that 50% of particles have a diameter in the order of 50 microns.

The memantine suspension prepared at the time by disintegrating the grooved tablets in water (Sample I) showed 50% of particles with an average diameter Tess than 50 microns and 90% with an average diameter less than 160.2 microns.

For memantine in suspension (Sample II) the D parameter (0.5) indicated that 50% of the particles are in the order of 45 microns and 90% of particles are less than 100 microns, conforming to parameter D (0.90).

For memantine in suspension prepared at the time from powder for suspension and adding water (Sample III), the assessment indicated that 50% of particles have an approximate diameter of 55 microns and 90% are less than 110 microns.

The memantine suspension made by grinding commercially available tablets for oral administering and adding water (Sample IV) differs significantly from the above values. Specifically:

50% of particles had a diameter over 90 microns (D 0.5) and 90% less than 211 or 217 microns.

Virtually the size of the particles formed by grinding commercially available oral tablets suspended in water, is 100% greater than the particles in the suspensions that this invention describes.

The invention claimed is:

1. A premixture of a pharmaceutical composition of memantine for oral administration, comprising:
   i) granulated pellets, the granulated pellets comprising memantine; pregelatinised corn starch, silicon dioxide and microcrystalline cellulose, wherein the memantine is present in an amount between 10 and 15% w/w of the premixture, wherein the granulated pellets are coated with:
      i.1) a first coating of polyvinylpyrrolidone, and
      i.2) a second coating comprising a cationic copolymer of dimethylaminoethyl methacrylate, butyl methacrylate and methyl methacrylate, wherein the cationic copolymer is present in an amount between 80 and 95% w/w of the second coating and magnesium stearate, wherein the magnesium stearate is present in an amount between 5 and 20% w/w of the second coating;
   ii) sucralose in an amount between 4 and 7% w/w of the premixture; and
   iii) one or more essences selected from the group consisting of: peppermint, lemon, cherry, raspberry, grapefruit, lime-lemon, and a combination of any two or more thereof, in an amount between 11 and 19% w/w of the premixture;
   wherein all the components of the premixture are particles which have a particle size smaller than 710 microns,
   wherein, in the presence of water, 90% of the particles in suspension have an average diameter less than 170 microns,
   and wherein, according to the dissolution assay in the Japanese Pharmacopoeia XV, the dissolution of memantine at a pH similar to the pH in the buccal cavity, at 15 seconds is less than 5%, at 30 seconds is lower than 10%, and at 60 seconds is less than 20%.

2. The premixture according to claim 1, wherein:
   ii) sucralose is in an amount between 4 and 7% w/w of the premixture;
   iii.1) peppermint essence is in an amount between 4 and 7% w/w of the premixture; and
   iii.2) lemon essence is in an amount between 7 and 12% w/w of the premixture.

3. The premixture according to claim 2, wherein:
   ii) sucralose in an amount between 5 and 5.5% w/w of the premixture;
   iii.1) peppermint essence in an amount between 5.5 and 6% w/w of the premixture; and
   iii.2) lemon essence in an amount between 10.5 and 11.5% w/w of the premixture.

4. The premixture according to claim 1, wherein:
   ii) sucralose is in an amount between 5.0 and 6.0% w/w total of the premixture; and
   iii) one or more essences is selected from the group consisting of: cherry essence, raspberry essence, and grapefruit essence in an amount between 11 and 19% w/w total of the premixture.

5. The premixture according to claim 1, wherein memantine is in an amount between 10 and 12% w/w of the premixture.

6. The premixture according to claim 1 characterized in that according to the dissolution assay in the Japanese Pharmacopoeia XV, the dissolution of memantine at a pH similar to the pH in the buccal cavity, at 15 seconds is null, at 30 seconds is lower than 5%, and at 60 seconds is less than 14%.

7. A pharmaceutical composition of memantine for oral administration, comprising a premixture according to claim 1.

8. A composition according to claim 7, characterized in that the composition is a suspension that comprises between 1.0 mg and 3.0 mg of memantine per millilitre of suspension, and 50% particles have an average diameter less than 50 microns and 90% particles have an average diameter less than 110 microns.

9. A composition according to claim 7, characterized in that the composition is a powder for the preparation of a suspension before administering, by adding water or another drink and stirring; wherein 50% of particles of the powder have an average diameter less than 60 microns and 90% have an average diameter less than 120 microns.

10. A composition according to claim 9, characterized in that the composition is packaged in single-dose sachets.

11. A composition according to claim 9, characterized in that the composition is packaged in multi-dose sachets.

12. A composition according to claim 10, characterized in that each single-dose unit comprises 5, 10, 15, or 20 milligrams of memantine.

13. A composition according to claim 7, characterized in that the composition is a grooved, orally disintegrating tablet comprising 5 or 10 or 20 milligrams of memantine.

14. A composition according to claim 13, characterized in that said tablet, suspended in water, forms a suspension of particles wherein 50% of particles have an average diameter less than 60 microns and 90% of the particles have an average diameter less than 170 microns.

15. A composition according to claim 13, characterized in that said tablet is an orally disintegrating tablet, suitable for administering directly without the help of water, so that with the saliva in the buccal cavity the tablet forms a suspension in less than 15 seconds.

16. A composition according to claim 13, characterized in that said tablet has an in vitro disintegrating time of 5 seconds, according to assay USP 32.

17. A composition according to claim 13, characterized in that according to the dissolution assay in the Japanese Pharmacopoeia, the dissolution of the memantine in the tablet at a pH similar to the buccal pH, after 15 seconds is less than 5%, after 30 seconds is less than 10%, and after 60 seconds is less than 20%; and according to assay USP 38 at a pH similar to the gastric pH the dissolution after 15 minutes is greater than 80%, and after 45 minutes is greater than 90%.

18. A procedure for preparing a premixture according to claim 1, comprising the following steps:
   a) preparing a homogeneous mixture of powders containing microcrystalline cellulose in an amount between 90 and 91.5% w/w of the mixture, pregelatinised corn starch in an amount between 7 and 8.5% w/w of the mixture and silicon dioxide in an amount between 0.5 and 1.5% w/w of the mixture;
   b) preparing a homogeneous suspension containing between 8.5 and 9.5% by a process having steps of:
      i) dissolving the memantine under stirring in an ethanol and water 70/30 mix, producing a solution,
      ii) adding pregelatinised starch in an amount of 5 to 7% by weight to the solution, and then adding polyethylene glycol 6000 in an amount between 1 and 4% by weight, to the solution,
      iii) stirring for no less than one hour to form the homogeneous suspension; with the percentages by weight being relative to the total weight of the suspension;
   c) granulating the homogeneous mixture of powders obtained in step a) in a fluid bed and top spraying, at a temperature less than 50° C., with the suspension containing the memantine obtained in step b), until pellets are formed, wherein the pellets contain an amount of memantine between 10 and 15% w/w of the premixture;
   d) coating the pellets with a first coating, wherein the first coating is applied to the pellets by top spraying a suspension of polyvinylpyrrolidone in an amount between 10 and 30% w/v in water, at a mixture temperature below 50° C.;
   e) coating the pellets obtained in step d) with a second coating, by bottom spraying a coating suspension comprising between 80 and 87% by weight of isopropyl alcohol, between 3.5 and 5.5% by weight of water, between 9 and 12.5% by weight of cationic copolymer of dimethylaminoethyl methacrylate, butyl methacrylate and methyl methacrylate and between 0.5 and 2% by weight of magnesium stearate, wherein the coating suspension is at a temperature between 25 and 30° C. throughout the bottom spraying, producing double-coated pellets;
   f) passing the double-coated pellets through a sieve to form granulated memantine pellets;
   g) mixing, for between 10 and 30 minutes:
   the granulated memantine pellets obtained in step f),
   sucralose, and
   one or more essences selected from the group consisting of: peppermint, lemon, cherry, raspberry, grapefruit, lime-lemon, and a combination of any two or more thereof, wherein the granulated pellets are present in an amount between 74 and 85% w/w, and contain the second coating which comprises between 80.0 and 90.0% w/w of cationic copolymer of dimethylaminoethyl methacrylate, butyl methacrylate, and methyl methacrylate, and between 5 and 20% w/w of magnesium stearate, the sucralose is present in an amount between 4 and 7% w/w, and the essences are present in an amount between 11 and 19% w/w, producing a product; and
   h) sieving the product of step g through a mesh size of 710 microns, discarding aggregates, thereby producing the premixture.

19. The procedure according to claim 18, characterized in that the coating suspension from step (e) comprises between 83.0 and 84.5% w/w of isopropyl alcohol, between 4.0 and 4.5% w/w of water, between 10.0 and 10.5% w/w of cationic copolymer of dimethylaminoethyl methacrylate, butyl methacrylate and methyl methacrylate and between 1.3 and 1.7% w/w of magnesium stearate.

20. The procedure for preparing a pharmaceutical composition of memantine for administering orally, comprising the following steps:
   preparing a premixture according to claim 18,
   preparing a homogeneous mixture of powders formed with:
      Microcrystalline cellulose, between 85 and 90% w/w total of the mixture;
      Sucralose, between 2 and 3% w/w total of the mixture;
      peppermint essence, between 1.3 and 2.7% w/w total of the mixture; and
      lemon essence, between 6.7 and 9.3% w/w total of the mixture;
   adding to said homogeneous mixture of powders between 13.5 and 16% by weight of said premixture,
   mixing and forming a further homogeneous mixture,
   adding to the further homogeneous mixture sugar in sufficient amount to obtain an end mixture that contains:
      the premixture, between 2.5 and 4.0% by weight total of the composition,
      sucralose, between 0.5 and 1% by weight total of the composition,
      peppermint essence, between 0.4 and 0.7% by weight total of the composition,
      lemon essence, between 1.6 and 3.0% by weight total of the composition,
      microcrystalline cellulose, between 20 and 21% by weight total of the composition,
      sugar, between 70 and 75% by weight total of the composition, and
   packaging the end mixture in single-dose or two compartment aluminium-aluminium sachets or in multi-dose phials.

21. A procedure for preparing a pharmaceutical composition of memantine for administering orally, comprising the following steps:
preparing a premixture according to claim 18;
preparing a homogeneous mixture of powders after passing each component through a sieve with a mesh size of 710 microns with:
Microcrystalline cellulose, between 87 and 88% w/w total of the homogeneous mixture of powders;
Sucralose, between 2.5 and 3.0% w/w total of the homogeneous mixture of powders;
Peppermint essence, between 1.80 and 2.0% w/w total of the homogeneous mixture of powders;
Lemon essence, between 7.7 and 8.0% w/w total of the homogeneous mixture of powders
adding to the mixture of powders between 14 and 15% by weight of the premixture,
mixing and forming a further homogeneous mixture,
adding to the further homogeneous mixture sugar in sufficient quantity to obtain an end mixture that contains:
the premixture, between 3.5 and 4.0% w/w total of the composition;
sucralose, between 0.6 and 1.0% w/w total of the composition;
peppermint essence, between 0.6 and 0.7% w/w total of the composition;
lemon essence, between 2.1 and 2.3% w/w total of the composition;
microcrystalline cellulose, between 20.3 and 20.7% w/w total of the composition;
sugar, between 72 and 74% w/w total of the composition; and
packaging the end mixture in single-dose or two compartment aluminium-aluminium sachets or in multi-dose phials.

22. A procedure for preparing a pharmaceutical composition of memantine for administering orally, comprising the following steps:
preparing a premixture according to claim 18,
preparing a homogeneous mixture of powders comprising:
microcrystalline cellulose, between 53 and 70% w/w total of the homogeneous mixture;
sucralose, between 0.2 and 0.9% w/w total of the homogeneous mixture;
lemon essence, between 2.2 and 3.5% w/w total of the homogeneous mixture;
methylparaben, between 1.5 and 2.3% w/w total of the homogeneous mixture;
propylparaben, between 0.1 and 0.3% w/w total of the homogeneous mixture;
adding an amount of the premixture to the homogeneous mixture, thereby forming an end mixture, wherein the amount of the premixture is between 26 and 40% w/w of the end mixture;
mixing to form a homogeneous end mixture, and
metering into a multi-dose phial with sufficient capacity for a permanent suspension with a content of 2.5 or 5 milligrams of memantine per millilitre formed previously by adding 120 millilitres of water to 8.44 or 16.88 grams of the homogeneous end mixture obtained and stirring, to administer to a patient a necessary volume of suspension according to an indicated posology.

23. A procedure for preparing a pharmaceutical composition of memantine for oral administration, comprising the following steps:
preparing a premixture according to claim 18,
preparing a homogeneous mixture comprising:
33.2 to 40.4% by weight of the premixture;
50 to 60% by weight of a coprocessed product made up of mannitol, starch, sodium croscarmellose, colloidal silica and silica;
5 to 7% by weight of cross-linked povidone;
0.1 to 0.3% by weight 0.16% of peppermint essence;
previously sieved through a mesh size of 710 microns and subsequently mixed in a cubic mixer for 15 to 30 minutes;
adding an amount of sodium stearyl fumarate thereby preparing an end mixture, wherein the amount of the sodium stearyl fumarate is between 1.7 and 2.3% by weight of-the end mixture and wherein the sodium stearyl fumarate was previously sieved through a mesh size of 250 microns,
mixing the end mixture for 5 minutes, forming a homogeneous end mixture,
compressing the homogeneous end mixture with a grooved punch, forming grooved tablets and packaging the grooved tablets in an aluminium-aluminium blister, wherein the disintegration time of each of the grooved tablets, according to assay USP 32 is 5 seconds after adding one of the grooved tablets to between 5 and 10 ml of water and stirring to form a suspension.

* * * * *